United States Patent [19]

Willis et al.

[11] 4,326,996

[45] Apr. 27, 1982

[54] FRAGRANCE COMPOSITION COMPRISING SUBSTITUTED CYCLOHEXANE DERIVATIVES

[75] Inventors: Brian J. Willis, Bergenfield, N.J.; Robert G. Eilerman, Merrick, N.Y.

[73] Assignee: Fritzsche Dodge & Olcott Inc., New York, N.Y.

[21] Appl. No.: 116,839

[22] Filed: Jan. 30, 1980

[51] Int. Cl.$^3$ .............................................. A61K 7/46

[52] U.S. Cl. ............................... 252/522 R; 131/276; 426/534; 560/231; 568/346; 568/376; 568/377; 568/667; 568/825; 568/828

[58] Field of Search .................... 252/522 R; 568/376, 568/377

[56] References Cited

U.S. PATENT DOCUMENTS

| | | | |
|---|---|---|---|
| 3,268,589 | 8/1966 | Rowland | 568/341 |
| 3,927,107 | 12/1975 | Schulte-Elte | 252/522 R |
| 4,130,508 | 12/1978 | Light et al. | 252/522 R |
| 4,246,292 | 1/1981 | Konst et al. | 252/522 R |

OTHER PUBLICATIONS

Schulte-Elte et al., Justus Liebigs Ann. Chem., 1975, 484.

*Primary Examiner*—John F. Niebling
*Attorney, Agent, or Firm*—Cooper, Dunham, Clark, Griffin & Moran

[57] ABSTRACT

The present invention relates to substituted cyclohexane derivatives having the structure:

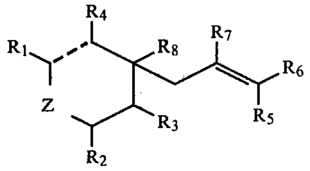

wherein the dotted line may be a carbon-carbon double bond or a carbon-carbon single bond; wherein $R_1$,$R_2$,$R_3$, $R_4$,$R_5$,$R_6$,$R_7$ and $R_8$ may be hydrogen or lower alkyl; wherein Z may be any of the following:

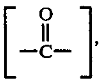

, 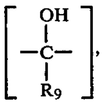 , 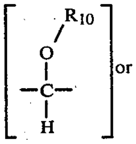 or 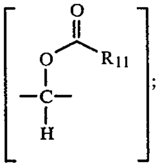 ;

wherein $R_9$ may be hydrogen or lower alkyl; and wherein $R_{10}$ and $R_{11}$ are lower alkyl. This invention also provides methods of preparing and using the compounds as odor-modifying ingredients in perfumes and perfumed products, and as flavor-modifying ingredients in foodstuffs and tobacco products.

5 Claims, No Drawings

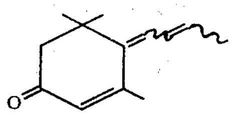

wherein the wavy lines represent "cis" or "trans" isomers which upon addition to tobacco impart "a pleasing flavor."

German Pat. Nos. 2,216,974 and 2,256,347 disclose a compound having the structure:

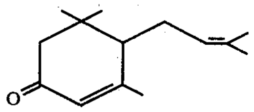

which is prepared by a process unrelated to that of the instant invention. U.S. Pat. No. 3,268,589 discloses compounds having the structures:

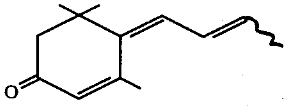

and

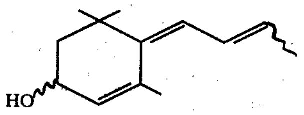

which impart a peppery, spicy odor to tobacco.

Although the compounds disclosed in U.S. Pat. Nos. 3,211,157 and 3,268,589 and German Pat. Nos. 2,216,974 and 2,256,347 have functional groups which are similar to the compounds of our invention, the sructures and organoleptic profiles are different in kind from the compounds of the instant invention.

Schulte-Elte, et al. Justus Liebigs Ann. Chem., 1975, 484 discloses the compound having the structure:

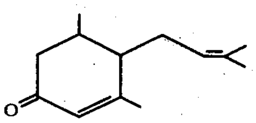

which was isolated from a reaction mixture as an unexpected minor by-product. No indication of utility or discussion of the organoleptic properties of the compound is given.

No prediction of the organoleptic properties of the compounds of the instant invention can be made by a study of the above-mentioned disclosures.

DETAILED DESCRIPTION OF THE INVENTION

It has been found that new and novel flavors and flavoring compositions, perfumes and perfumed articles, as well as tobacco products, can be successfully produced by adding effective amounts of one or more of the substituted cyclohexane and cyclohexane derivatives having the structural formula:

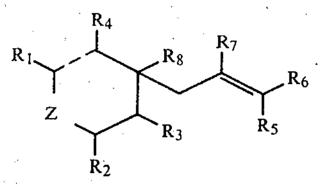

wherein the dotted line may be a carbon-carbon double bond or a carbon-carbon single bond; wherein $R_1$,$R_2$,$R_3$,$R_4$, $R_5$,$R_6$,$R_7$ and $R_8$ may be hydrogen or lower alkyl; wherein Z may be any of the following:

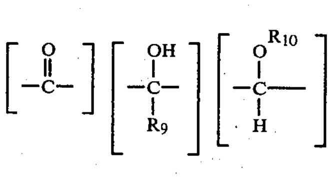

or

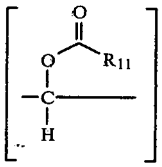

wherein $R_9$ may be hydrogen or lower alkyl; and wherein $R_{10}$ and $R_{11}$ may be lower alkyl.

The substituted cyclohexane and cyclohexene derivatives of the present invention have been found to possess distinctive balsamic, amber-like, woody, sweet, rooty, musty, earthy, leathery, green, citrus, herbaceous, floral odors which are useful in fine fragrances as well as perfumed products such as soaps, detergents, deodorants, cosmetic preparations and the like.

One or more of the substituted cyclohexanes and cyclohexenes of this invention and auxiliary perfume ingredients, for example, alcohols, aldehydes, ketones, nitriles, esters and essential oils, may be admixed so that the combined odors of the individual components produce a desired fragrance. Such perfume compositions are carefully balanced harmonious blends of essential oils, aroma chemicals, resinoids and other extracts of natural odorous materials. Each ingredient imparts its own characteristic effect in the composition. Thus, one or more of the substituted cyclohexanes and cyclohexenes of this invention can be employed to impart novel characteristics in fragrance compositions.

Such compositions may contain up to about 80 weight percent of any one or more of the substituted cyclohexanes and cyclohexenes of this invention. Ordinarily, at least about 0.001 weight percent of the substituted cyclohexane or cyclohexene is required to impart significant odor characteristics. Amounts in the range from about 1 to about 60 weight percent are preferred. The substituted cyclohexanes and cyclohexenes of this invention may be formulated into concentrates containing from about 1 to about 60 weight percent in an appropriate solvent. Such concentrates are then employed to formulate products such as colognes, soaps, etc., wherein the concentration of the compounds of this invention can be in the range of from about 0.001 to about 7 weight percent, depending upon the final product. For example, the concentration of the chemicals of this invention will be from about 0.001 to about 0.01 to about 7 weight percent in perfumes and colognes.

The substituted cyclohexanes and cyclohexenes of this invention are useful as olfactory components of perfume compositions for detergents and soaps; space odorants and deodorants; perfumes, colognes; toilet water; bath preparations such as bath oils and bath

FRAGRANCE COMPOSITION COMPRISING SUBSTITUTED CYCLOHEXANE DERIVATIVES

BACKGROUND OF THE INVENTION

There is an increased demand for materials which can be utilized to impart, alter or enhance the flavor and/or fragrance of consumable items. The natural oils which have traditionally been used for this purpose often suffer the disadvantages of limited supply, high cost, and variable quality.

Accordingly, the search for synthetic materials which can function as partial or total replacements for essentials oils, or which can find use in the creation of new and unique flavor and fragrance materials has intensified in recent years.

Various substituted cyclohexane derivatives have been disclosed in the prior art. For example, Arctander, *Perfume and Flavor Chemicals,* Vols. 1 & 2, (1969) provides the following illustrative examples of such compounds which have use in perfume and flavor compositions:

(1) "433: para-tertiary-BUTYL CYCLOHEXANOL

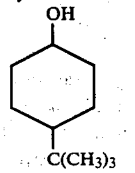

Extremely dry, woody-camphoraceous, almost "tarry" odor with leather-like undertone.

Used in perfume compositions to lend power and diffusiveness to soap fragrances, along with woody notes, Ionones, Cedarwood oil derivatives, etc. and with the acetate of this alcohol. It is stable in soap and does not discolor in mixtures with any common perfume chemical."

(2) "580: laevo-CARVONE
(1)-1-Methyl-4-iso-propenyl-6-cyclohexen-2-one. para-Methadien-6,8(9)-one-(2).

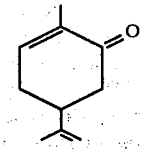

Warm-herbaceous, breadlike, penetrating and diffusive odor, somewhat spicy, in extreme dilution also floral, overall reminiscent of Spearmint Oil (rectified).

Warm and sweet, spicy, refreshing minty taste.

Occasionally used in perfume compositions, particularly in floral bases, where it introduces enormous power and often lends pleasing natural notes to the fragrance. However, it demands great skill and experience in application. It seems to constitute a very good and compatible companion to Rose Oxide and the Jasmone chemicals.

Extensively used in flavor compositions, mainly as a powerful spearmint note, to fortify Spearmint oil, etc. in hard candy, chewing gum, toothpaste and many kinds of candy. Furthermore, in Mint flavor blends, spice blends, liquor flavors, etc."

(3) "1020: 2,4-DIMETHYL-6-iso-HEXYL CYCLOHEXANONE

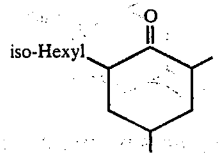

Powerful green-orrisy, slightly woody odor. Rather dry without being pronounced "camphoraceous."

(4) "1749: 1-HYDROXY-2-METHYL-4-tertiary-AMYLCYCLOHEXANE.
ortho-Methyl-para-tertiary-amylcyclohexane.

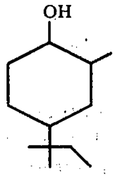

Woody-rootlike, dry-sweet and very tenacious odor with resemblance to Vetiver, Cedar and Amyris.

This material has been suggested for use in perfume compositions, where it may introduce a supporting note to Vetiver and precious wood notes, furthermore give "lift" and stable power particularly in soap perfumes. It blends excellently with the Ionones and Methylionones, with Cedarwood derivatives and musks, and with Oakmoss products."

(5) "3001: 1,1,3-TRIMETHYL-2-CYCLOHEXENONE-4.
2,4,4-Trimethyl-2-cyclohexen-1-one.

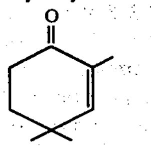

Powerful and rather pungent, but in dilution pleasant, warm-herbaceous and minty-camphoraceous odor, reminiscent of Tansy oil or Dalmation Sage oil.

The title ketone has been suggested for use in perfume compositions, and if it became available in a state of higher olfactory purity and quality, it could well be used in modern soap and detergent fragrances, perfumes for household products, etc." *Chemical Abstracts,* Vol. 68, 39828e (abstract of L. M. Shulov, et al., Zh. Org. Khim. 1967, 3, 1819) discloses the preparation of the compound:

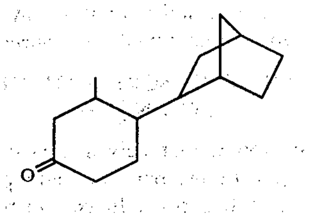

having the fragrance of fresh greens.

U.S. Pat. No. 3,211,157 discloses the preparation of compounds having the following structure:

solids; hair preparations such as lacquers, brilliantines, pomades and shampoos; cosmetic preparations such as creams, deodorants, hand lotions and sunscreens; powders such as talcs, dusting powders and face powders; and the like.

Because of their unique organoleptic properties, the substituted cyclohexanes and cyclohexenes of this invention have also been found to have utility in the alteration of the flavor component or components of flavor compositions. They can be used effectively to impart a certain natural character to artificial flavors. They can also be employed successfully to modify the organoleptic properties of such consumables as chewing gums, beverages, pharmaceutical preparations, fruit juices and the like.

The flavoring properties of the substituted cyclohexanes and cyclohexenes of this invention depend upon the type of products to which they are added. They develop woody, earthy, minty, fruity, citrusy flavor notes or combinations thereof. They can be employed advantageously in certain citrus products such as orange oil to round off the taste and in grape flavors where the taste and aroma are markedly enhanced.

Again, the proportions of the substituted cyclohexanes and cyclohexenes of this invention can vary within a wide range of concentrations depending upon the organoleptic properties desired. Typically, particularly interesting flavor effects can be obtained with concentrations of about 0.001 to about 1 weight percent of the compound in the final flavor composition. In some situations higher concentrations of the substituted cyclohexanes and cyclohexenes are required to produce special flavoring effects. For example, when used in artificial flavor compositions they may be incorporated at levels of 20 weight percent or more.

When one or more of the substituted cyclohexanes or cyclohexenes of this invention is added to smoking tobacco or synthetic tobacco, they impart woody, amber-like, and cedarwood notes to the tobacco aroma. The proportions are preferably between 1 to 100 ppm, but in certain situations higher levels may be usefully employed.

The description of the practice of the instant invention set forth above is meant to illustrate its usefulness and is in no way intended to limit the scope of the invention.

In accordance with one of the embodiments of the present invention, the compounds of the invention can be prepared by one of several processes. In some of the processes outlined hereinbelow the starting material is an appropriately substituted 2,4-dioxocyclohexane carboxylate having the structural formula:

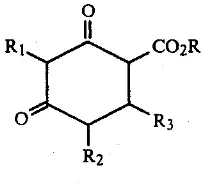

I wherein $R_1$,$R_2$, and $R_3$ are as defined hereinabove; and R is methyl or ethyl, preferably, methyl. Specific examples of carboxylates (I) falling within the scope of the foregoing structural formula include the following:

Methyl 2,4-dioxo-3-methylcyclohexane carboxylate
Methyl 2,4-dioxo-5-methylcyclohexane carboxylate
Methyl 2,4-dioxo-6-methylcyclohexane carboxylate
Methyl 2,4-dioxo-3,5-dimethylcyclohexane carboxylate
Methyl 2,4-dioxo-3,6-dimethylcyclohexane carboxylate
Methyl 2,4-dioxo-5,6-dimethylcyclohexane carboxylate
Methyl 2,4-dioxo-3,5,6-trimethylcyclohexane carboxylate
Methyl 2,4-dioxo-3-methyl-5-ethylcyclohexane carboxylate
Methyl 2,4-dioxo-3-methyl-6-ethylcyclohexane carboxylate
Methyl 2,4-dioxo-3-methyl-5,6-diethylcyclohexane carboxylate
Methyl 2,4-dioxo-5-methyl-3-ethylcyclohexane carboxylate
Methyl 2,4-dioxo-5-methyl-6-ethylcyclohexane carboxylate
Methyl 2,4-dioxo-5-methyl-3,6-diethylcyclohexane carboxylate
Methyl 2,4-dioxo-6-methyl-3-ethylcyclohexane carboxylate
Methyl 2,4-dioxo-6-methyl-5-ethylcyclohexane carboxylate
Methyl 2,4-dioxo-6-methyl-3,5-diethylcyclohexane carboxylate
Methyl 2,4-dioxo-3,5,6-triethylcyclohexane carboxylate
Methyl 2,4-dioxo-3-methyl-5-propylcyclohexane carboxylate
Methyl 2,4-dioxo-3-methyl-6-propylcyclohexane carboxylate
Methyl 2,4-dioxo-3-methyl-5,6-dipropylcyclohexane carboxylate
Methyl 2,4-dioxo-5-methyl-3-propylcyclohexane carboxylate
Methyl 2,4-dioxo-5-methyl-6-propylcyclohexane carboxylate
Methyl 2,4-dioxo-5-methyl-3,6-dipropylcyclohexane carboxylate
Methyl 2,4-dioxo-6-methyl-3-propylcyclohexane carboxylate
Methyl 2,4-dioxo-6-methyl-5-propylcyclohexane carboxylate
Methyl 2,4-dioxo-6-methyl-3,5-dipropylcyclohexane carboxylate
Methyl 2,4-dioxo-3,5,6-tripropylcyclohexane carboxylate
Methyl 2,4-dioxo-3-methyl-5-isopropylcyclohexane carboxylate
Methyl 2,4-dioxo-3-methyl-6-isopropylcyclohexane carboxylate
Methyl 2,4-dioxo-3-methyl-5,6-diisopropylcyclohexane carboxylate
Methyl 2,4-dioxo-5-methyl-3-isopropylcyclohexane carboxylate
Methyl 2,4-dioxo-5-methyl-6-isopropylcyclohexane carboxylate
Methyl 2,4-dioxo-5-methyl-3,6-diisopropylcyclohexane carboxylate
Methyl 2,4-dioxo-6-methyl-3-isopropylcyclohexane carboxylate
Methyl 2,4-dioxo-6-methyl-5-isopropylcyclohexane carboxylate
Methyl 2,4-dioxo-6-methyl-3,5-diisopropylcyclohexane carboxylate
Methyl 2,4-dioxo-3,5,6-triisopropylcyclohexane carboxylate
Methyl 2,4-dioxo-3-ethylcyclohexane carboxylate
Methyl 2,4-dioxo-5-ethylcyclohexane carboxylate
Methyl 2,4-dioxo-6-ethylcyclohexane carboxylate Methyl 2,4-dioxo-3-ethyl-5-propylcyclohexane carboxylate
Methyl 2,4-dioxo-3-ethyl-6-propylcyclohexane carboxylate
Methyl 2,4-dioxo-3-ethyl-5,6-dipropylcyclohexane carboxylate
Methyl 2,4-dioxo-5-ethyl-3-propylcyclohexane carboxylate
Methyl 2,4-dioxo-5-ethyl-6-propylcyclohexane carboxylate
Methyl 2,4-dioxo-5-ethyl-3,6-dipropylcyclohexane carboxylate
Methyl 2,4-dioxo-6-ethyl-3-propylcyclohexane carboxylate
Methyl 2,4-dioxo-6-ethyl-5-propylcyclohexane carboxylate
Methyl 2,4-dioxo-6-ethyl-3,5-dipropylcyclohexane carboxylate
Methyl 2,4-dioxo-3-propylcyclohexane carboxylate
Methyl 2,4-dioxo-5-propylcyclohexane carboxylate
Methyl 2,4-dioxo-6-propylcyclohexane carboxylate
Methyl 2,4-dioxo-3-propyl-5-isopropylcyclohexane carboxylate
Methyl 2,4-dioxo-3-propyl-6-isopropylcyclohexane carboxylate
Methyl 2,4-dioxo-3-propyl-5,6-diisopropylcyclohexane carboxylate
Methyl 2,4-dioxo-5-propyl-3-isopropylcyclohexane carboxylate
Methyl 2,4-dioxo-5-propyl-6-isopropylcyclohexane carboxylate
Methyl 2,4-dioxo-5-propyl-3,6-diisopropylcyclohexane carboxylate
Methyl 2,4-dioxo-6-propyl-3-isopropylcyclohexane carboxylate
Methyl 2,4-dioxo-6-propyl-5-isopropylcyclohexane carboxylate
Methyl 2,4-dioxo-6-propyl-3,5-diisopropylcyclohexane carboxylate Some of these are known compounds and to the extent that they are new, known methods such as those diagrammed in Scheme A can be employed for their production.

Scheme A

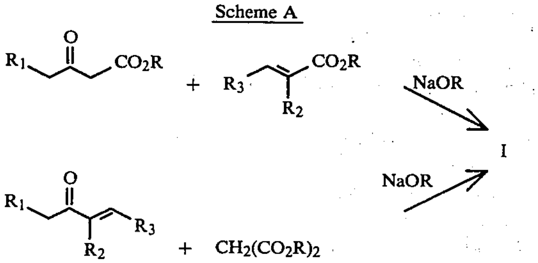

Process 1

The appropriate 2,4-dioxocyclohexane carboxylate (I) is subjected to enol ether formation by treatment with a lower alkanol, preferably isopropanol in the presence of an acidic catalyst such as a mineral acid or p-toluenesulfonic acid and a hydrocarbon solvent such as benzene, toluene, xylene and the like with azeotropic removal of water (as disclosed in German Pat. No. 2,335,080) resulting in a compound with the structure:

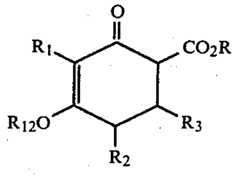

II wherein $R_{12}$ is lower alkyl, preferably, isopropyl or isobutyl.

The carboxylate II is reacted with an olefin compound having the structure:

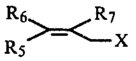

wherein X is a halogen selected from the group consisting of chloro, bromo, and iodo thereby forming an alkylated carboxylate having the structure:

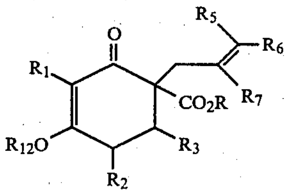

III

The above transformation may be accomplished, for example, by first forming the enolate of the carboxylate (II) with an alkali metal hydride such as sodium hydride or potassium hydride in an inert solvent such as benzene, toluene, xylene, tetrahydrofuran, dimethoxyethane, dimethylformamide, hexamethylphosphoric triamide, or dimethyl sulfoxide. The enolate is then treated with the olefinic halide at temperatures in the range from about 0° to 120° C., the temperature range from about 20° to 40° C. being preferred. Although either compound may be used in excess, the preferred molar ratio of olefinic halide to carboxylate is from about 1:1 to about 1.2:1. Reaction times of from about 1 to 15 hours are required depending upon the temperature and solvent utilized, with higher temperatures resulting in decreased reactions times.

Alternatively, the reaction may be carried out in the presence of a phase transfer catalyst. Specific examples of phase transfer catalysts useful in the present invention include benzyltriethylammonium chloride, cetyltrimethylammonium chloride, and tricaprylmethylammonium chloride. The alkylation of carboxylate II with the olefinic halide is carried out in the presence of approximately one equivalent of a base such as an alkali metal hydride, alkoxide, or hydroxide in an inert solvent such as benzene, toluene, xylene, hexane, or methylene chloride. Temperatures in the range from about 20° to 150° C. may be employed, the temperature range from about 30° to 100° C. being preferred. The amount of phase transfer catalyst based on carboxylate II may vary from about 0.1 to 10 mole percent, the preferred amount being in the range from about 0.5 to 5 mole percent.

The alkylated carboxylate III is then decarboxylated by heating it in the presence of an alkali metal salt in a polar, aprotic solvent such as dimethylsulfoxide, hexamethylphosphoric triamide, 1-methyl-2-pyrrolidone, or dimethylformamide resulting in production of a cyclic ketone having the structure:

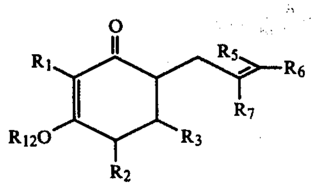

IV wherein the substituents are as set forth hereinabove. Preferred metal salts include lithium chloride, lithium bromide, lithium iodide, sodium chloride, sodium iodide, and sodium cyanide. The reaction is desirably carried out at temperatures from about 80° to 160° C., with temperatures in the range from about 100° to 140° C. being preferred.

It is desirable that the mole ratio of carboxylate: alkali metal salt be from about 1:1 to 1:10, preferably from about 1:1.5 up to about 1:2.

The cyclic ketone IV may then be further transformed by any one or a combination of the steps outlined in Scheme B to obtain the compounds of the instant invention.

SCHEME B

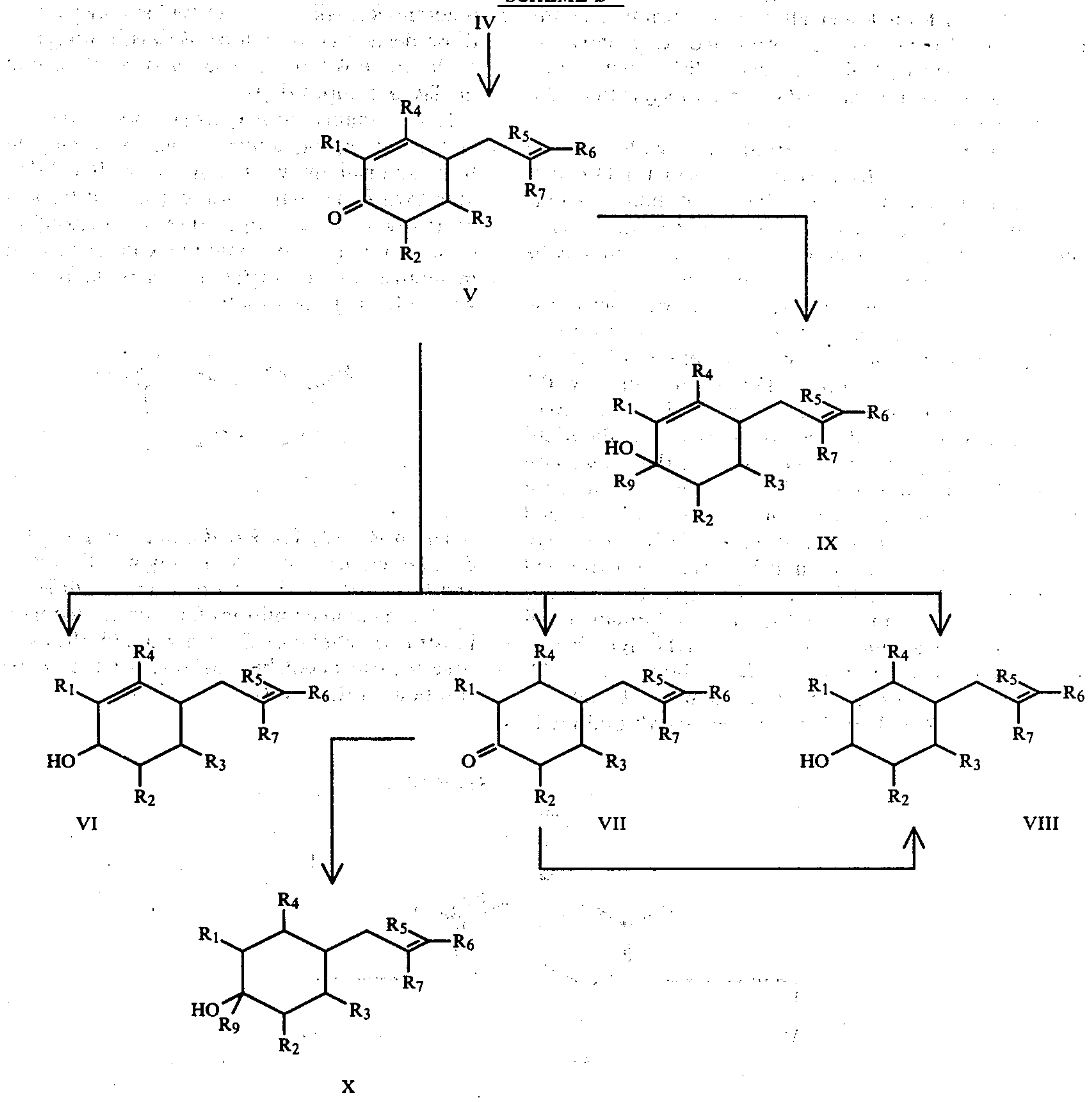

In accordance with the transformations illustrated by Scheme B hereinabove, the ketone IV may be reacted with an organometallic derivative such as a Grignard reagent (e.g. $R_4MgX$) or an organolithium compound (e.g., $R_4Li$) wherein $R_4$ is lower alkyl. The reaction with the organometallic is desirably carried out with a stoichiometric quantity of the reagent when the lithium derivative is utilized or with excess organometallic (2 to 3 equivalents) when a Grignard reagent is employed. The reaction is preferably carried out in inert solvents such as diethyl ether, tetrahydrofuran, or mixtures of diethyl ether or tetrahydrofuran in benzene, toluene, or hexane. It is preferred to carry out the reaction in an inert atmosphere such as nitrogen or argon at temperatures in the range from about 0° C. to 50° C. The resulting organometallic adduct is then hydrolyzed with a dilute aqueous acid such as hydrochloric acid. The hydrolyzed product may be isolated by solvent extraction and purified by fractional distillation to give the substituted 2-cyclohexene-1-one, V. This ketone may be utilized in perfume or flavor compositions or further modified.

The ketone V may be treated with a Grignard reagent $R_9MgX$ such as $CH_3MgI$ or an organolithium $R_9Li$ wherein $R_9$ is lower alkyl under reaction conditions essentially the same as those stated hereinabove. In this instance, the hydrolysis is accomplished with either ice-cold aqueous mineral acid or preferably with a saturated ammonium chloride solution.

Reduction of the ketone group in V with an alkali metal aluminum hydride such as diisobutylaluminum hydride at about 0° C. in an inert solvent such as hexane or toluene followed by hydrolysis under neutral conditions gives the corresponding alcohol VI which may be utilized in perfume or flavor compositions.

The hydrogenation of ketone V is carried out in the presence of a metal catalyst such as palladium on carbon, copper chromite, or Raney nickel in an inert solvent such as a lower alcohol. Dilute solutions (e.g. 0.1 to 0.5 molar) of an alkali metal hydroxide in a lower alkanol such as ethanol at temperatures from about 20° C. to 50° C. are particularly desirable for the conversion to the cyclohexanone VII. Purification by fractional distillation results in a compound which may be utilized in perfume or flavor compositions or further modified.

The reduction of compound VII may be performed using standard methodology, for example, by means of an alkali metal aluminum hydride such as lithium aluminum hydride in an inert solvent such as diethyl ether or tetrahydrofuran at temperatures from about 0° C. to 30° C. Alternatively, a boron hydride such as sodium borohydride in a lower alkanol may be employed resulting in the preparation of compound VIII. This material may be utilized in perfume or flavor compositions or reacted with an organometallic compound such as a Grignard reagent (e.g., $R_9MgX$) or an organolithium $R_9Li$ wherein $R_9$ is lower alkyl under conditions similar to those described for ketone V thus leading to formation of the alcohol X which itself may be utilized in perfume or flavor compositions.

In accordance with another embodiment of the present invention, the ketone group in IV may be reduced with an alkali aluminum hydride such as lithium aluminum hydride in an inert solvent such as tetrahydrofuran or diethyl ether at temperatures from about 0° C. to 40° C. which, after hydrolytic work-up employing a dilute mineral acid such as HCl, results in the formation of the ketone having the structure:

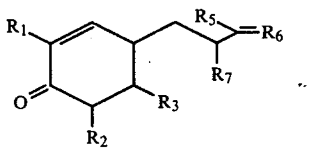

XI wherein $R_1$, $R_2$, $R_3$, $R_5$, $R_6$, and $R_7$ have the meaning defined above. This ketone may be utilized in perfume and flavor compositions or further modified.

The reaction conditions for the transformations of XI illustrated in Scheme C are essentially the same as those described in detail hereinabove for the corresponding reaction in Scheme B.

SCHEME C

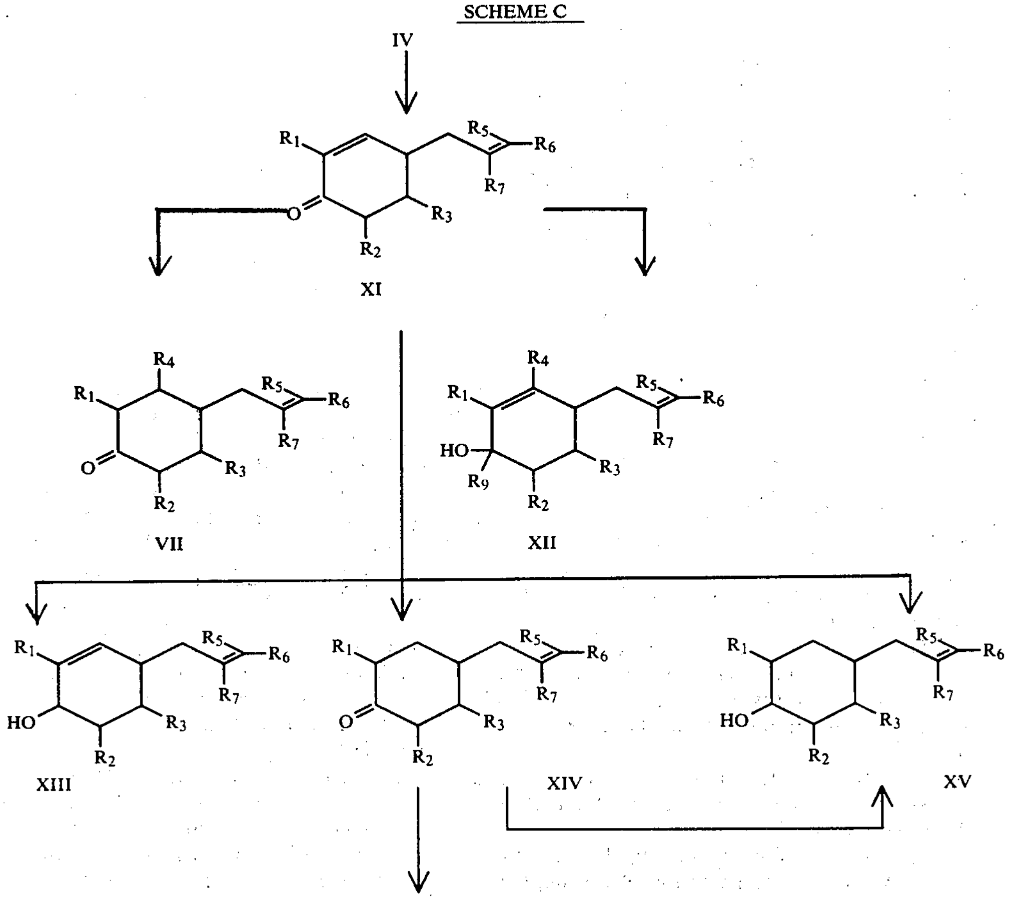

IV

XI

VII

XII

XIII

XIV

XV

-continued

SCHEME C

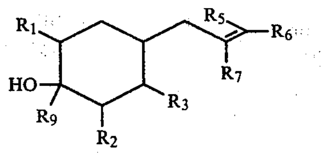

XVI

In addition, the cyclohexenone XI may be reacted with an organometallic reagent such as $(R_4)_2$ LiCu or a Grignard reagent $R_4MgX$ in the presence of a catalytic amount of a copper salt, i.e. curous iodide, wherein $R_4$ is lower alkyl according to known methods (see, for example, Posner, *Organic Reactions,* Vol. 19, p 1, (1972). Temperatures in the range from about −30° to 10° C. are typically employed and the solvent may be either diethyl ether or tetrahydrofuran. Reaction times from about 1 to 10 hours are required and hydrolysis using an aqueous mineral acid results in a compound having the structural formula:

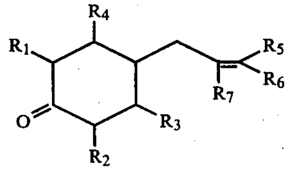

VII

The alcohols VI, VIII, XIII and XV may, in addition, be subjected to esterification in accordance with standard techniques (see, L. F. Fieser and M. Fieser, *Reagents for Organic Synthesis,* Vol. I, p 958 (1967). For example, esterification with an alkanoic acid anhydride such as acetic anhydride or propionic anhydride or treatment with an acyl halide, preferably an acyl chloride in the presence of an organic base such as N,N-dimethylaniline to form compounds having the structure:

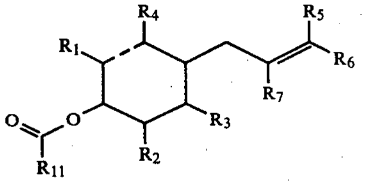

XVII wherein $R_4$ is hydrogen or lower alkyl; wherein $R_{11}$ is lower alkyl; and wherein the dotted line represents a carbon-carbon double bond or a carbon-carbon single bond.

In accordance with a further embodiment of the present invention, the alcohol group in compounds VI, VIII, XIII and XV may be transformed by etherification to compounds having the structure:

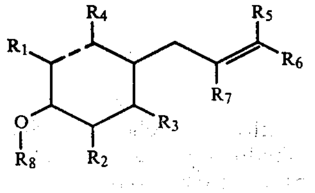

XVIII wherein $R_4$ is hydrogen or lower alkyl; wherein $R_8$ is lower alkyl; and wherein the dotted line represents a carbon-carbon double bond or a carbon-carbon single bond. The transformation may be effected by known techniques (see J. March, *Advanced Organic Chemistry,* 2nd ed., p. 357, (1977). For example, the alcohol may be treated with an alkali metal hydride such as sodium hydride in an inert solvent followed by alkylation of the resulting alkoxide with either an alkyl halide $R_8X$ (e.g. $CH_3I$) or an alkyl sulfate $(R_8)_2SO_4$ (e.g. $(CH_3)_2SO_4$) to generate the compounds of formula XVIII.

Process 2

The appropriately substituted 1,3-cyclohexanedione enol ether having the structure:

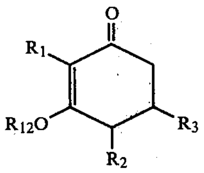

XIX wherein $R_1$, $R_2$, $R_3$, and $R_{12}$ have the meaning set forth hereinabove may likewise be reacted with an olefinic compound having the structure:

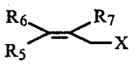

wherein X is a halogen chosen from chloro, bromo, or iodo and each of $R_5$, $R_6$, and $R_7$ are hydrogen or lower alkyl.

Alkylation, following a known procedure (J. Org. Chem., 38, 1775 (1973)) may be accomplished by first forming the kinetic enolate with an alkali metal salt of a secondary amine such as lithium diisopropylamide or lithium isopropylcyclohexylamide in an inert solvent such as diethyl ether, tetrahydrofuran, or mixtures of tetrahydrofuran or diethyl ether with hexamethylphosphoric triamide. The alkylation is carried out at temperatures from about −70° to −50° C. after which the reaction mixture is allowed to warm to 20°-25° C. Reaction times can range from 2 to 15 h. depending upon the solvent and olefinic halide employed. The compound thus formed having the structure:

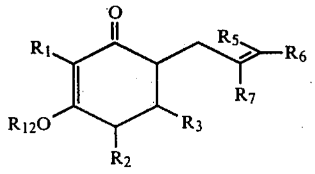

IV may be treated in the same manner as the identical compound described in Process 1 and illustrated in Schemes B and C.

In accordance with a further embodiment of the present invention, the ketone IV may be treated with an alkali metal salt of a secondary amine such as lithium diisopropylamide or lithium isopropylcyclohexylamide as described hereinabove for compound XIX. Altkylation of the resulting enolate may be accomplished with an alkyl halide $R_8X$ wherein X may be chloro, bromo, or iodo at temperatures from about −60° C. to −40° C. after which the reaction mixture is allowed to warm to about 20° C. to 25° C. Reaction times can range from about 10 to 25 hours depending upon the solvent and halide employed. The compound thus formed having the structure:

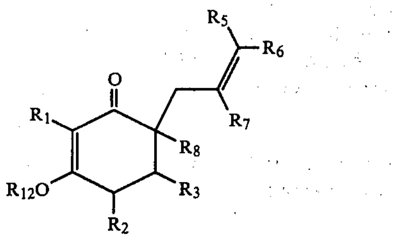

XX may be further transformed as described for the similar compound of Process 1 and illustrated in Schemes B and C.

Isolation and purification of the final products of the present invention is achieved by conventional techniques which include extraction, distillation, crystallization, preparative chromatographic separation and the like.

It will be recognized that the compounds of the present invention can exist in several stereoisomeric forms, including the "R" and "S", as well as the "cis" and "trans" isomers. The foregoing structural formulae are intended to embrace the individual stereoisomers as well mixtures of the various stereoisomers of the substituted cyclohexances and cyclohexenes of this invention.

The following examples are set forth to more fully illustrate the practices of this invention, but are in no way meant to limit the scope thereof.

EXAMPLE 1

Methyl 2-oxo-4-isopropoxy-6-methyl 3-cyclohexene carboxylate

A mixture of methyl 2,4-dioxo-6-methylcyclohexane carboxylate (184 g, 1 mol), isopropanol (96 g, 1.6 mol) and p-toluenesulfonic acid (2 g) in benzene (600 mL) was heated at reflux for 6 hours with azeotropic removal of water. After cooling, the solution was washed several times with 5% sodium carbonate solution and the benzene then removed on a rotary evaporator. Short path distillation gave 171.6 g of the carboxylate, bp 110°-112° C./0.05 mm.

IR (film): 1750, 1665, 1610 $cm^{-1}$.

NMR ($CDCl_3$): 1.08(3H, d, J=5.5 Hz), 1.32 (6H, d, J=6 Hz), 2.0-2.9(3H,m), 3.1(1H,dd), 3.8(3H,s), 4.5(1H, h, J=6 Hz), 5.42(1H,bs)δ.

EXAMPLE 2

Methyl 1-(3-methyl-2-butenyl)-2-oxo-4-isopropoxy-6-methyl-3-cyclohexane carboxylate

Method A

To a stirred suspension of sodium hydride (50% dispersion, 0.15 mol) in anhydrous dimethylformamide (120 mL) under a nitrogen atmosphere was added methyl 2-oxo-4-isopropoxy-6-methyl-3-cyclohexene carboxylate (29.4 g, 0.13 mol; produced according to Example 1), dropwise over 30 minutes while maintaining the temperature between 30° and 35° C. After addition was complete, the temperature was held at 40° C. for 1 hour and then prenyl bromide (22.3 g, 0.15 mol; prepared by the method of Tetrahedron, 33, 580 (1977) in dimethylformamide (20 mL) was added followed by stirring for 16 hours at room temperature. The reaction mixture was poured into water (300 mL) and extracted with ether. The ether extracts were washed with water, brine, and dried ($Na_2SO_4$). Removal of the solvent gave 34.5 g of methyl carboxylate which was used without further purification. Kugelrohr distillation (bath temperature 125° C./0.05 mm) of a small sample gave material with the following spectral data:

IR (film): 1745, 1660, 1610 $cm^{-1}$.

NMR ($CDCl_3$): 0.95(3H,2d), 1.25(6H,d), 1.62(6H,2s), 2-2.9(5H,complex), 3.62(3H,s), 4.4(1H,h), 4.8(1H,m), 5.4(1H,bs)δ.

MS: 294(M+), 193, 151, 69, 159, 177.

Method B

Sodium hydride (50% dispersion, 0.06 mol) was freed of mineral oil and suspended in toluene (20 mL) under a nitrogen atmosphere. The suspension was heated to 75° C. and methyl 2-oxo-4-isopropoxy-6-methyl-3-cyclohexene carboxylate (11.3 g, 0.05 mol) in an equal volume of toluene was added. Heating was continued for 1 hour and then Aliquate 336® (0.2 g, previously dried by azeotropic removal of water) was added along with prenyl bromide (8.2 g, 0.055 mol). The mixture was heated at 75°-80° C. for 4 hours and then cooled to room temperature. Several milliliters of methanol were added and the reaction mixture poured into 100 mL of water. The toluene layer was washed with water and the solvent removed on a rotary evaporator to give 13 g of a crude amber colored oil. Short path distillation gave 7.1 g of alkylated carboxylate, bp 111°-118° C./0.05 mm.

EXAMPLE 3

3-Isopropoxy-5-methyl-6-(3-methyl-2-butenyl)-2-cyclohexen-1-one

Reaction

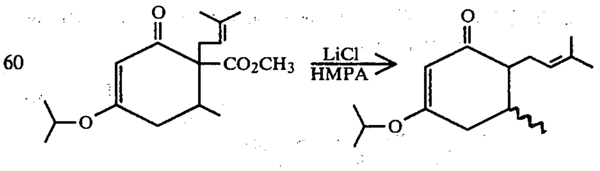

To a solution of methyl 1-(3-methyl-2-butenyl)-2-oxo-4-isopropoxy-6-methyl-3-cyclohexene carboxylate (29.4 g, 0.1 mol) in anhydrous hexamethylphosphoric triamide (220 mL) was added anhydrous lithium chloride (6.4 g, 0.15 mol). The mixture was stirred at 130° C. in a nitrogen atmosphere for 1.5 hours and then added to water (800 mL). The aqueous solution was extracted with ether. The combined ether extracts were washed with water and dried ($Na_2SO_4$). The ether was removed on a rotary evaporator and the residue vacuum distilled, yielding 20.1 g of 3-isopropoxy-5-methyl-6-(3-methyl-2-butenyl)-2-cyclohenen-1-one, bp 104°-108° C./0.05 mm. The product was shown by glc/ms to be a mixture of "cis" and "trans" isomers in a ratio of 76:24.

IR(film): 1660, 1610 $cm^{-1}$.

NMR($CDCl_3$): 1.0(3H,2d), 1.28(6H,d,J=6 Hz), 1.65(6H, bs), 1.9-2.7(6H,m), 4.45(1H,h,J=6 Hz), 5.1(1H,m), 5,35(1H,s)δ.

MS: 236(M+), 69, 111, 126, 84, 168.

EXAMPLE 4

3,5-Dimethyl-4-(3-methyl-2-butenyl)-2-cyclohexen-1-one

Reaction

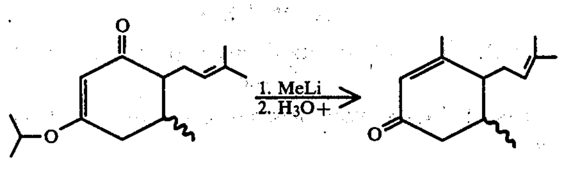

To a solution of 3-isopropoxy-5-methyl-6-(3-methyl-2-butenyl)-2-cyclohexen-1-one (11.8 g, 0.05 mol) in ether (150 mL) at 0° C. was added ethereal methyllithium (28 mL, 0.06 mol) over a period of 15 minutes. The mixture was allowed to warm to room temperature and stirred for 2 hours. 2 N aqueous hydrochloric acid solution (400 mL) was added and stirring continued at room temperature for 1 hour. The organic layer was separated, washed with aqueous sodium bicarbonate and dried ($Na_2SO_4$). Removal of the solvent and distillation of the residue gave 7.8 g of enone, bp 65°-68° C./0.01 mm as a mixture of two isomers by glc/ms (74% and 23%).

IR(film): 1670, 1628 $cm^{-1}$.

NMR($CCl_4$): 1.0(3H,2d), 1.65(6H,2bs), 1.92(3H,d), 1.8-2.6(6H,m), 5.05(1H,m), 5.7(1H,bs)δ.

MS: 192(M+), 109, 69, 124, 110, 77.

EXAMPLE 5

A perfume composition was prepared by mixing the following:

| | % |
|---|---|
| Vanillin | 0.5 |
| Coumarin | 3.0 |
| Musk ketone | 4.5 |
| Geraniol | 3.0 |
| Oil Geranium | 1.5 |
| Benzyl acetate | 7.5 |
| Oil Cedarwood | 3.0 |
| Cedryl acetate | 9.0 |
| Hydroxycitronellal | 12.0 |
| Benzyl salicylate | 4.5 |
| Isoamyl salicylate | 4.5 |
| Oil Ylang extra | 3.0 |
| Oil Clary Sage | 1.5 |
| Oil Orange Sweet Flor. | 1.5 |
| Oil Lavender Barreme | 1.5 |
| Oil Bergamot rect. | 4.5 |
| Linalool synthetic | 3.0 |
| Linalyl acetate synthetic | 1.5 |
| Methyl dihydrojasmonate | 3.0 |
| Oil Sandalwood, East Indian | 3.0 |
| Cinnamic alcohol ex Styrax | 0.5 |
| Phenylethyl acetate | 0.5 |
| Phenylethyl alcohol | 2.0 |
| Ionone alpha | 0.5 |
| Gamma undecalactone 10% | 0.5 |
| Rose oxide 10% | 0.5 |
| Oil Nutmeg 10% | 0.5 |
| Oil Patchouly | 0.5 |
| Jasmin Absolute, Italian | 3.0 |
| Oil Neroli | 0.5 |
| laevo Carvone 10% | 0.5 |
| Diethyl phthalate | 9.0 |
| 3,5-Dimethyl-4-(3-methyl-2-butenyl)-2-cyclohexen-1-one | 6.0 |
| | 100.0 |

EXAMPLE 6

3-Ethyl-4-(3-methyl-2-butenyl)-5-methyl-2-cyclohexen-1-one

Reaction

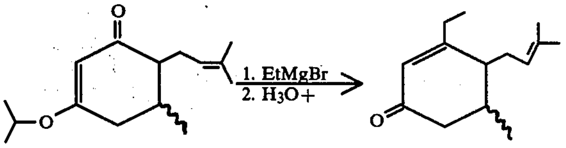

Ethyl bromide (14.1 g, 0.13 mol) in absolute diethyl ether (20 mL) was added under nitrogen to magnesium turnings (3.1 g, 0.13 g-atom) at a rate sufficient to maintain gentle reflux. To this solution was added 3-isopropoxy-5-methyl-6-(3-methyl-2-butenyl)-2-cyclohexen-1-one (10 g, 0.042 mol) in absolute diethyl ether (15 mL) dropwise over 40 minutes. The reaction mixture was refluxed for an additional 3 hours. The cooled mass was cautiously added to 2 N hydrochloric acid (250 mL) and stirred to toom temperature for 1 hour. The organic layer was separated and the aqueous extracted with two 50 mL portions of diethyl ether. The extracts were combined, washed with saturated sodium bicarbonate, and dried ($Na_2SO_4$). Solvent removal and distillation gave 5.6 g of enone, bp 99°-107° C./0.5 mm. The product is a mixture of two isomers (ca. 70:30) as indicated by glc/ms.

IR(film): 1670, 1630 $cm^{-1}$.

NMR($CDCl_3$): 1.05(6H, t superimposed on broad d), 1.65(6H,2bs), 1.8-2.6(8H,m), 5.1(1H,m), 5.85(1H,bs)δ.

MS: 206(M+), 109, 138, 69, 123, 95.

EXAMPLE 7

4-(3-Methyl-3-butenyl)-5-methyl-2-cyclohexen-1-one

Reaction

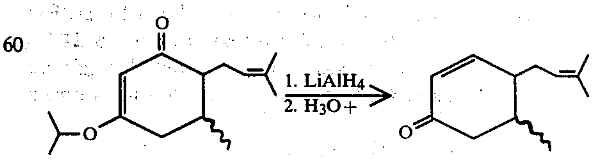

To a stirred suspension of lithium aluminum hydride (1.9 g, 0.05 mol) in anhydrous diethyl ether (250 mL) at 0° C. was added 3-isopropoxy-5-methyl-6-(3-methyl-2-butenyl)-2-cyclohexen-1-one (11.8 g, 0.05 mol) in diethyl ether (20 mL). The mixture was stirred for 1.5 hour and then ethyl acetate (22 g) was added slowly to destroy excess hydride. Water (10 ml) was added and the mixture warmed to room temperature. The solution was filtered and added with stirring to 2 N hydrochloric acid (200 mL). After 1 hour the organic layer was separated and the aqueous extracted once with diethyl ether. The combined ether layers were washed with saturated sodium bicarbonate solution and dried ($Na_2SO_4$). Solvent removal and distillation through an 8 cm micro Vigreaux column gave 8.4 g of enone, bp 99°-101° C./1 mm (2 isomers by glc/ms analysis).

IR(film): 1675, 1630 $cm^{-1}$.

NMR($CCl_4$): 1.05 (3H.bd), 1.62(6H,2s), 1.8-2.6(6H,m), 5.15(1H,m), 5.9(1H, broadended d,J=10.5 Hz), 6.78(1H, broadened, d,J=10.5 Hz)δ.

MS: 178(M+), 69, 110, 95, 41.

EXAMPLE 8

3,5-Dimethyl-4-allyl-2-cyclohexen-1-one

Reaction A

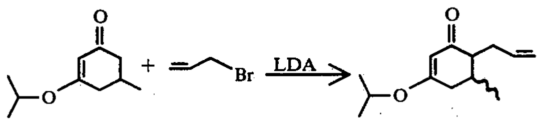

Reaction B

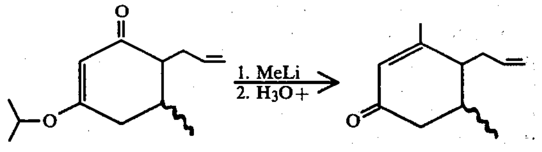

Procedure A

To a solution of dry diisopropylamine (15 g, 0.145 mol) in anhydrous tetrahydrofuran (100 mL) under a nitrogen atmosphere was added a 2.5 M hexane solution of n-butyllithium (58 mL), with stirring at −20° C. The solution was cooled to −70° C. and hexamethylphosphoric triamide (27 g) was added, followed after 30 minutes by dropwise addition of 3-isopropoxy-5-methyl-2-cyclohexen-1-one (23.5 g, 0.14 mol) in, tetrahydrofuran (30 mL). After 40 minutes allylbromide (18.1 g, 0.15 mol) in an equal volume of tetrahydrofuran was added dropwise over 20 minutes. The cooling bath was removed and the temperature allowed to rise to 25° C. Stirring was continued for 2 hours followed by addition of water (5 mL) and removal of the solvent on a rotary evaporator. The residue was dissolved in diethyl ether, washed with water and brin, and dried ($Na_2SO_4$). Solvent removal and fractional distillation afforded 24.1 g of alkylated ketone, bp 125°-130° C./1 mm. The glc/ms analysis demonstrated the presence of two isomers (ratio of 84:16).

IR(film): 1655, 1620 $cm^{-1}$.

NMR($CDCl_3$): 1.1(3H,2d), 1.3(6H,d,J=6 Hz), 1.8-2.7(6H,m), 4.45(1H,h,J=6 Hz), 5.05(2H, m), 5.32(1H,bs), 5.8(1H,m)δ.

MS: 208(M+), 84, 82, 69, 151, 85.

Procedure B

A solution of 3-isopropoxy-5-methyl-6-allyl-2-cyclohexen-1-one (16.6 g, 0.08 mol) in anhydrous diethyl ether (300 mL) was cooled to 0° C. under nitrogen and 1.6 M ethereal methyllithium (56 mL, 0.09 mol) added. The mixture was stirred for 2 hours and methanol added to destroy any excess methyllithium. The reaction mixture was mixed with 2 N aqueous hydrochloric acid (400 mL) and stirred for 1 hour. The reaction mixture was then extracted with diethyl ether and the ether extracts washed with saturated sodium bicarbonate solution. The extracts were dried ($Na_2SO_4$) and concentrated on a rotary evaporator. The crude oil was fractionally distilled to give 11.4 g of enone, bp 88°-90° C./1.5 mm, as a mixture of 2 isomers (glc/ms analysis).

IR(film): 1670, 1630, 915 $cm^{-1}$.

NMR($CDCL_3$): 1.05(3H,2d), 2.0(3H,d), 2.1-2.75(6H,m), 5.1(2H,m), 5.75(1H,m), 5.85(1H,bs)δ.

MS: 164(M+), 95, 79, 67, 93, 77.

EXAMPLE 9

3,5-Dimethyl-4-(2-methyl-2-propenyl)-2-cyclohexen-1-one

Essentially the same process as Example 8 was employed.

Procedure A

The alkylation with methallyl chloride required overnight reaction at room temperature for completion. Purification was accomplished by initial short path distillation, followed by chromatography on 500 g of silica gel, eluting with hexaneethyl acetate 85:15. In this manner 12.5 g of 3-isopropoxy-5-methyl-6-(2-methyl-2-propenyl)-2-cyclohexen-1-one was obtained having the structure:

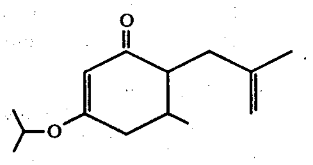

IR(film): 1660, 1620 $cm^{-1}$.

NMR($CDCl_3$): 1.05(3H,2d), 1.3(6H,d,J=6 Hz), 1.75(3H,bs), 1.9-2.6(6H,m), 4.45(1H,h,J=6 Hz), 4.78(2H,m) 5.3(1H,s)δ.

Procedure B Treatment of 3-isopropoxy-5-methyl-6-(2-methyl-2-propenyl)-2-cyclohexen-1-one (5.6 g, 0.025 mol) with 1.6 M methyllithium (0.03 mol) in diethyl ether gave, after hydrolysis, 4.4 g of 3,5-dimethyl-4-(2-methyl-2-propenyl)-2-cyclohexen-1-one, bp 120°-125° C./1 mm, having the structure:

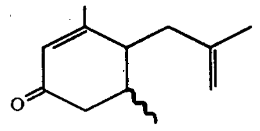

Again two isomers were present, as determined by glc/ms analysis.

IR(Film); 1670, 1620 $cm^{-1}$.

NMR($CDCl_3$): 1.02(3H,bd), 1.78(3H,bs), 2.0(3H,d), 2.1–2.8(6H,m), 4.8(2H,m), 5.85(1H,bs)δ.

MS: 178(M+), 95, 94, 122, 93, 79.

EXAMPLE 10

3,5-Dimethyl-4-(2-butenyl)-2-cyclohexen-1-one Prepared by the same process as Example 8.

Procedure A

Alkylation was accomplished with commercial crotyl chloride (contains 20% 3-chloro-1-butene) overnight at room temperature. Isolation and short path distillation afforded 14.1 g of a product which was 81% pure. Chromatography on 500 g of silica gel, eluting with hexane-ethyl acetate 80:20, gave 9.2 g of 3-isopropoxy-5-methyl-6-(2-butenyl)-2-cyclohexen-1-one having the structure:

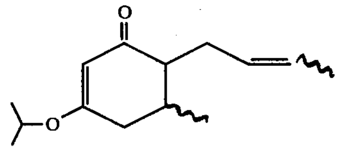

IR: 1660, 1615 $cm^{-1}$.

NMR: 1.08(3H,bd), 1.3(6H,d,J=6 Hz), 1.65(3H,m), 1.8–2.7(6H,m), 4.45(1H,J=6 Hz), 5.35(1H,s), 5.45(2H,m)δ.

MS: 222(M+), 84, 165, 111, 125, 69).

Procedure B

Treatment of the 3-isopropoxy-5-methyl-6-(2-butenyl)-2-cyclohexen-1-one (5.6 g, 0.025 mol) with 1.6 M methyllithium (0.03 mol) in diethyl ether gave after acid hydrolysis 3.3 g of 3,5-dimethyl-4-(2-butenyl)-2-cyclohexen-1-one, bp 125°–130° C./1 mm, having the structure:

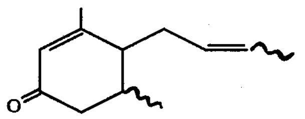

Glc/ms analysis indicated the presence of four isomers (ratio 57:17:20:6).

IR(film): 1670, 1625, 970 $cm^{-1}$.

NMR($CDCl_3$): 1.05(3H,bd), 1.65(3H,m), 2.0(3H,d,J=1.5 Hz), 2.35(6H,m), 5.46(2H,m), 5.85(1H,bs)δ.

MS (major isomer): 178(M+), 109, 124 95, 79, 55.

EXAMPLE 11

3,5-Dimethyl-4-(3-methyl-2-butenyl)cyclohexanone

Reaction

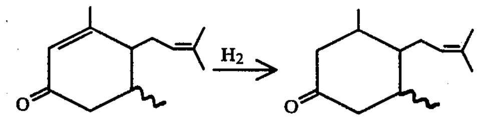

A solution of 3,5-dimethyl-4-(3-methyl-2-butenyl)-2-cyclohexen-1-one (8.2 g, 0.043 mol) in 0.3 M ethanolic KOH (16 mL) was hydrogenated at room temperature and 1 atmosphere over 5% palladium on carbon (0.8 g). After uptake of 1 equivalent of hydrogen, the solution was filtered through Celite and concentrated. The residue was partitioned between hexane and water; then the hexane layer was dried ($Na_2SO_4$) and the solvent removed on a rotary evaporator. Kugelrohr distillation gave 7.3 g of 3,5-dimethyl-4-(3-methyl-2-butenyl) cyclohexanone, bp 115° C./0.5 mm.

IR(film): 1720 $cm^{-1}$.

NMR($CDCl_3$): 1.0(6H, two overlapping d), 1.7(6H,2bs), 1.8–2.6(9H,m), 5.18(1H,m)δ.

MS: 194(M+), 69, 124, 55, 83, 82.

EXAMPLE 12

3,5-Dimethyl-4-(3-methyl-2-butenyl)-cyclohexanol

Reaction

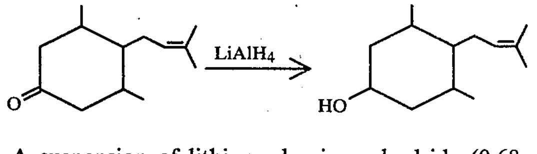

A suspension of lithium aluminum hydride (0.68 g, 0.018 mol) in anhydrous diethyl ether (50 mL) was stirred under nitrogen at 10° C. while 3,5-dimethyl-4-(3-methyl-2-butenyl) cyclohexanone (6.8 g, 0.035 mol) in anhydrous ether (15 mL) was added over a period of 30 minutes. The mixture was stirred at room temperature for 2 hours; then it was treated successively with $H_2O$ (0.7 mL), 15% NaOH (0.7 mL), and $H_2O$ (2.1 mL). The solution was filtered, dried ($NaSO_4$), and concentrated to give the crude alcohol as a colorless oil. Kugelrohr distillation afforded 6.2 g of 3,5-dimethyl-4-(3-methyl-2-butenyl) cyclohexanol, bp 130° C./0.3 mm.

IR(film): 3350 $cm^{-1}$.

NMR($CDCl_3$): 0.95(6H, overlapping doublets), 1.3–2.4(16H, m with superimposed broadened absorptions at 1.65 and 1.7), 3.6(1H,m), 5.08(1H,m)δ.

MS: 196(M+), 109, 67, 69, 107, 83.

EXAMPLE 13

3,5-Dimethyl-4-(3-methyl-2-butenyl)-2-cyclohexen-1-ol

Reaction:

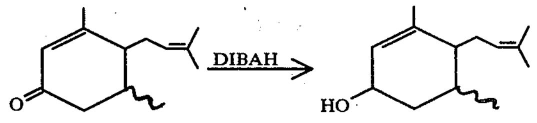

A solution of 3,5-dimethyl-4-(3-methyl-2-butenyl)-2-cyclohexen-1-one (4 g, 0.02 mol) in hexane (25 mL) was stirred under nitrogen at 0° C. and 1 M diisobutylaluminum hydride (25 mL) was added dropwise over 30 minutes. The mixture was stirred for 2 hours and methanol (60 mL) added to precipitate the salts. The solution was filtered and washed with 15% hydrochloric acid, saturated sodium bicarbonate and brine. Drying ($Na_2SO_4$), and solvent removal, followed by Kugelrohr distillation gave 3.8 g of 3,5-dimethyl-4-(3-methyl-2-butenyl)-2-cyclohexen-1-ol, bp 135°–140° C./0.5 mm.

IR(film): 3320, 1650 $cm^{-1}$.

NMR($CDCl_3$): 0.95(3H,2d), 1.65(6H,2bd), 1.7–2.6(7H,m), 4.1(1H,m), 5.0(1H,m), 5.5(1H,m)δ.

MS: (major isomer): 194(M+), 107, 133, 91, 109, 69.

EXAMPLE 14

A fougere type perfume composition was prepared by mixing the following:

| | % |
|---|---|
| Coumarin | 5.0 |
| Musk Ambrette | 5.0 |
| Musk aldehyde FDO | 5.0 |
| Methylionone gamma | 4.0 |
| Isoamyl salicylate | 4.0 |
| Oil Galbanum | 0.5 |
| Delta decalactone (1% in diethyl phthalate) | 0.5 |
| Santol FDO | 4.0 |
| Oil Patchouly | 6.0 |
| Oakmoss absolute incolore | 4.0 |
| Oil Neroli-Base | 7.0 |
| Oil Geranium Maroc | 10.0 |
| Phenylethyl alcohol | 3.0 |
| Oil Bergamot | 7.0 |
| Linalool synthetic | 6.0 |
| Oil Lavender 50-52% | 10.0 |
| Eugenol extra | 2.0 |
| Isoeugenol | 1.0 |
| Benzyl benzoate | 4.0 |
| 3,5-Dimethyl-4-(3-methyl-2-butenyl)-2-cyclohexen-1-ol | 12.0 |
| | 100.0 |

EXAMPLE 15

A wood base was prepared by mixing the following:

| | |
|---|---|
| Coumarin | 4.0 |
| Olibanum resinoid | 2.0 |
| Oil Guaiacwood | 4.0 |
| Methylionone gamma | 8.0 |
| Santol FDO | 2.0 |
| Para-tertiarybutylcyclohexyl acetate | 2.0 |
| Isopropyl quinoline 10% | 4.0 |
| Oil Patchouly | 2.0 |
| Linalool synthetic | 2.0 |
| Oil Bergamot terpeneless | 4.0 |
| Oil Cedarwood | 12.0 |
| Cedryl acetate | 22.0 |
| Acetyl cedrene | 24.0 |
| 3,5-Dimethyl-4-(3-methyl-2-butenyl)-cyclohexanone | 8.0 |
| | 100.0 |

EXAMPLE 16

A floral bouquet was prepared by mixing the following:

| | % |
|---|---|
| Musk ketone | 1.0 |
| Coumarin | 1.0 |
| Methyl everninate | 0.5 |
| Oakmoss absolute | 0.5 |
| Geraniol | 10.0 |
| Phenylethyl alcohol | 16.0 |
| Citronellol | 2.0 |
| Geranyl acetate | 1.0 |
| Indole 10% | 1.0 |
| Rose otto | 3.0 |
| Rose oxide 10% | 1.0 |
| Hydroxycitronellal | 14.0 |
| Pentadecanolide | 1.0 |
| Methyl dihydrojasmonate | 10.0 |
| Hexyl cinnamic alcohol | 10.0 |
| Benzyl acetate | 1.0 |
| Oil Ylang extra | 0.5 |
| Cinnamic alcohol | 0.5 |

-continued

| | % |
|---|---|
| Phenylethyl acetate | 0.5 |
| Gamma undecalactone 10% | 0.5 |
| Cyclamen aldehyde | 0.5 |
| Ionone alpha | 0.5 |
| Methylionone gamma | 4.0 |
| Cedroxyde | 4.0 |
| Acetyl cedrene | 8.0 |
| Oil Bergamot rect. | 3.0 |
| 3,5-Dimethyl-4-(3-methyl-2-butenyl) | 5.0 |
| cyclohexanone | 100.0 |

EXAMPLE 17

A perfume composition was prepared by mixing the following:

| | % |
|---|---|
| Oakmoss absolute Yugoslav | 4.0 |
| Coumarin | 3.0 |
| Musk ketone | 6.0 |
| Musk ambrette | 2.0 |
| Ionone alpha | 2.0 |
| Methylionone gamma | 2.5 |
| Cinnamic alcohol | 2.5 |
| Oil Sandalwood, East Indian | 5.0 |
| Acetyl cedrene | 7.5 |
| Oil Patchouly | 1.0 |
| Amylcinnamic aldehyde | 1.0 |
| Benzyl acetate | 2.5 |
| Oil Olibanum 10% | 1.0 |
| Heliotropin | 1.0 |
| Oil Styrax | 1.0 |
| Isoeugenol | 0.5 |
| Hydroxycitronellal | 0.5 |
| Ethyl vanillin | 0.5 |
| Labdanum absolute | 0.5 |
| Oil Lemon | 1.0 |
| Oil Orange sweet Flor. | 4.0 |
| Benzyl alcohol | 2.0 |
| Pehnylethyl alcohol | 2.5 |
| Phenyl acetaldehyde 10% | 1.0 |
| Rose absolute | 2.5 |
| Oil Geranium | 2.5 |
| Jasmin absolute, Italian | 5.0 |
| Oil Neroli, Moroccan | 0.5 |
| Aldehyde C 10 10% | 1.0 |
| Aldehyde C 11 undecylenic 10% | 4.0 |
| Aldehyde C 12 MNA 10% | 2.0 |
| Oil Bergamot rect. | 20.0 |
| 4-(3-Methyl-2-butenyl)-5-methyl-2-cyclohexen-1-one | 8.0 |
| | 100.0 |

EXAMPLE 18

The following raspberry flavor was prepared

| | |
|---|---|
| Acetic acid | 0.1 |
| Gamma undecalactone | 0.1 |
| Benzyl acetate | 0.1 |
| Oil Buchu | 0.1 |
| Maltol | 0.2 |
| 4-(p-Hydroxyphenyl)-2-butanone | 1.0 |
| Ethyl acetate | 3.0 |
| Ethyl butyrate | 1.0 |
| Hexyl acetate | 1.5 |
| Ionone beta | 0.5 |
| Irone alpha, 1% in alcohol | 0.7 |
| Hexanal | 0.8 |
| Ethyl alcohol | 90.9 |
| | 100.0 |

This formulation was added to water, sugar and acid at the level of 10 ppm, and 3,5-dimethyl-4-(3-methyl-2-butenyl)cyclohexanol was added at a concentration of 1 ppm. The flavor which contained the substituted cyclohexanol was much preferred over a control. It added a smooth, woody character to the formulation and produced a more natural raspberry flavor.

EXAMPLE 19

3,5-Dimethyl-4-(3-methyl-2-butenyl)cyclohexanone (alternate method) CL Reaction

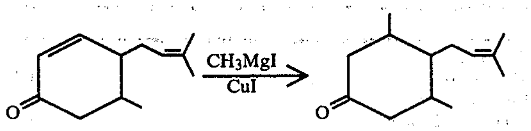

Cuprous iodide (0.52 g, 0.003 mol) was added at −5° C. to a Grignard solution prepared from magnesium (1.45 g, 0.06 mol) and methyl iodide (8.5 g, 0.06 mol) in anhydrous ether (30 mL) under nitrogen. The reaction mixture was stirred for 20 minutes and then 4-(3-methyl-2-butenyl)-5-methyl-2-cyclohexen-1-one (5.3 g, 0.03 mol, prepared according to Example 7) in ether (10 mL) was added dropwise. The mixture was stirred at 0° C. for 2 hours and then quenched into saturated $NH_4Cl$ solution (300 mL) which was made slightly basic by the addition of $NH_4OH$. The aqueous solution was extracted with ether, and the combined extracts washed with water and dried ($Na_2SO_4$). Solvent removal and Kugelrohr distillation gave 4.7 g of ketone, bp 115° C./0.5 mm.

Spectral data agreed with that reported for Example 7.

EXAMPLE 20

1,3,5-Trimethyl-4-(3-methyl-2-butenyl)-2-cyclohexen-1-ol

Reaction

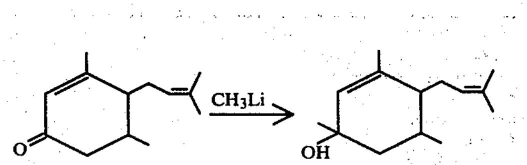

A solution of 3,5-dimethyl-4-(3-methyl-2-butenyl)-2-cyclohexen-1-one (2.9 g, 0.015 mol), prepared according to Example 4, in anhydrous tetrahydrofuran (20 mL), was cooled to 0° C. under nitrogen and 1.6 M ethereal methyllithium (10 mL) added dropwise. The solution was allowed to warm to room temperature and stirred for 4 hours. The reaction mixture was poured into ammonium chloride solution and extracted with ether. The ether extracts were washed with water, brine and dried ($Na_2SO_4$). Solvent removal and kugelrohr distillation (bath temperature 95°–100° C./0.1 mm) gave 2.8 g of the alcohol.

IR(film): 3400, 1665 $cm^{-1}$.

NMR($CDCl_3$): 1.05(3H,m), 1.25(3H,s), 1.55–2.65(16H,m), 5.0(1H,m), 5.4(1H,m)δ.

MS: 190(M-18), 121, 105, 93, 147, 69.

EXAMPLE 21

A chypre type perfume composition was prepared by mixing the following:

| | % |
|---|---|
| Oil Angelica Root | 0.5 |
| Castoreum absolute | 0.5 |
| Oil Rose | 1.0 |
| Civet absolute | 1.0 |
| Oakmoss absolute | 1.0 |
| Musk Ambretee | 2.0 |
| Labdanum resinoid | 3.0 |
| Oil Ylang extra | 5.0 |
| Benzyl acetate | 6.0 |
| Oil Sandalwood | 7.0 |
| Vanillin | 6.0 |
| Benzyl alcohol | 9.0 |
| Jasmin extract | 12.0 |
| Coumarin | 12.0 |
| Phenylethyl alcohol | 12.0 |
| Oil Bergamot | 20.0 |
| 4-(3-Methyl-2-butenyl)-5-methyl-2-cyclohexen-1-one | 2.0 |
| | 100.0 |

EXAMPLE 22

A lavender fragrance was prepared by mixing the following:

| | % |
|---|---|
| Oakmoss absolute | 1.0 |
| Musk xylene | 4.0 |
| Oil Rosemary | 5.0 |
| Oil Petitgrain Paraguay | 3.0 |
| Benzyl acetate | 5.0 |
| Oil Bois de Rose | 7.0 |
| Coumarin | 10.0 |
| Terpinyl acetate | 10.0 |
| Oil Spike Lavender | 20.0 |
| Oil Lavandin | 30.0 |
| 3-Ethyl-4-(3-methyl-2-butenyl)-5-methyl-2-cyclohexen-1-one | 5.0 |
| | 100.0 |

EXAMPLE 23

A jasmin fragrance was prepared by mixing the following:

| | % |
|---|---|
| Gamma undecalactone | 0.5 |
| p-Cresyl phenylacetate | 0.5 |
| Ethyl cinnamate | 0.9 |
| Oil Ylang | 7.0 |
| Geranyl acetate | 6.0 |
| Amylcinnamic aldehyde | 5.0 |
| Linalool synthetic | 10.0 |
| Benzyl acetate | 20.0 |
| Phenylethyl alcohol | 20.0 |
| Hydroxycitronellal | 30.0 |
| 3,5-Dimethyl-4-(2-butenyl)-2-cyclohexen-1-one | 0.1 |
| | 100.0 |

EXAMPLE 24

An oil vetiver substitute was prepared by mixing the following:

| | % |
|---|---|
| Oil Patchouly | 1.0 |
| Geraniol ex Palmarosa | 1.0 |
| Ionone residue | 3.0 |

-continued

| | % |
|---|---|
| Oil Copaiba | 12.0 |
| Cedryl acetate | 13.0 |
| Oil Guaicwood | 16.0 |
| Oil Cedarwood | 15.0 |
| Terpineol | 5.0 |
| Oil Bois de Rose | 9.0 |
| 3,5-Dimethyl-4-(3-methyl-2-butenyl)-cyclohexanol | 25.0 |
| | 100.0 |

EXAMPLE 25

Modification of an orange flavor:

| | % |
|---|---|
| Orange Oil Florida | 96.7 |
| 3,5-Dimethyl-4-(3-methyl-2-butenyl)-2-cyclohexen-1-one | 3.3 |
| | 100.0 |

This modified orange flavor was tested at the level of 30 ppm in a standard beverage medium consisting of sugar, acid and water. Whereas the straight orange oil at 30 ppm had the expected orange flavor, the modified flavor containing 3,5-dimethyl-4-(3-methyl-2-butenyl)-2-cyclohexen-1-one at the level of 1 ppm in the formulation was decidedly grapefruit in character.

EXAMPLE 26

The following cinnamon flavor compositions were prepared:

| | A(%) | B(%) |
|---|---|---|
| Salicylic aldehyde | 0.1 | 0.1 |
| Oil Ginger | 0.3 | 0.3 |
| o-Methoxycinnamic aldehyde | 0.1 | 0.1 |
| o-Methoxybenzaldehyde | 0.1 | 0.1 |
| Methyl salicylate | 0.5 | 0.5 |
| Terpineol alpha | 2.0 | 2.0 |
| Eugenol | 2.0 | 2.0 |
| Ionone beta | 0.5 | 0.5 |
| Cinnamic aldehyde | 91.1 | 94.4 |
| 3,5-Dimethyl-4-(3-methyl-2-butenyl) cyclohexanone | 3.3 | 0.0 |
| | 100.0 | 100.0 |

The above cinnamon flavor formulations were tasted at a level of 30 ppm. Composition A which contained 3,5-dimethyl-4-(3-methyl-2-butenyl) cyclohexanone successfully reduced the harshness of the cinnamic aldehyde. It resulted in a softer, more natural flavor.

EXAMPLE 27

The following grape base was prepared:

| | % |
|---|---|
| Gamma undecalactone | 0.2 |
| Ionone beta | 0.8 |
| Ethyl oenanthate | 1.0 |
| Ethyl methylphenylglycidate | 1.0 |
| Cinnamic alcohol | 3.0 |
| Methylnaphthyl ketone | 3.0 |
| Methyl anthranilate | 35.0 |
| Ethyl acetate | 56.0 |
| | 100.0 |

The above grape flavor was tasted at 30 ppm in a beverage base (sugar, water and acid). Then 3,5-dimethyl-4-(3-methyl-2-butenyl)-2-cyclohexen-1-one was added at the level of 1 ppm. The flavor developed by the grape base containing the added ketone was much preferred. The harsh acidic taste of the base was subdued and overall resulted in a better Concord flavor.

EXAMPLE 28

A fougere type perfume composition was prepared by mixing the following:

| | % |
|---|---|
| Coumarin | 3.0 |
| Musk ketone | 4.0 |
| Musk ambrette | 6.0 |
| Isoamyl salicylate | 8.0 |
| Vanillin from lignin | 2.0 |
| Oil Geranium Maroc | 3.0 |
| Oil Patchouly | 3.0 |
| Phenylethyl alcohol | 3.0 |
| Geraniol | 6.0 |
| Oil Bergamot | 10.0 |
| Heliotropin | 3.0 |
| Oakmoss absolute incolore | 2.0 |
| Anisic aldehyde | 1.0 |
| Santol FDO | 2.0 |
| Oil Lavender 50–52% | 8.0 |
| Linalool synthetic | 7.0 |
| Eugenol extra | 2.0 |
| Oil Lemon Italian | 10.0 |
| Lilial | 6.0 |
| Benzyl benzoate | 8.0 |
| 3,5-Dimethyl-4-(3-methyl-2-butenyl)2-2 cyclohexen-1-one | 3.0 |
| | 100.0 |

EXAMPLE 29

A violet perfume composition was prepared by mixing the following:

| | % |
|---|---|
| Musk ambrette | 0.6 |
| Jasmine absolute | 0.3 |
| Violet leaves absolute | 0.1 |
| Heliotropin | 1.0 |
| Methylionone | 3.0 |
| Benzoin Siam | 2.0 |
| Oil Cedarwood | 20.0 |
| Oil Sandalwood | 30.0 |
| Oil Orris Root | 40.0 |
| 3,5-Dimethyl-4-(3-methyl-2-butenyl) cyclohexanol | 3.0 |
| | 100.0 |

EXAMPLE 30

A fougere type perfume composition was prepared by mixing the following:

| | % |
|---|---|
| Undecyclenic aldehyde | 0.2 |
| Civet absolute | 0.3 |
| Vanillin | 0.5 |
| Rose Otto | 0.5 |
| Acetophenone | 0.5 |
| Anisic aldehyde | 1.0 |
| Oil Clary Sage | 1.0 |
| Isoamyl salicylate | 2.0 |
| Oil Patchouly | 2.0 |
| Jasmin absolute | 3.0 |

-continued

| | % |
|---|---|
| Oil Sandalwood | 3.0 |
| Linalool synthetic | 4.0 |
| Courmarin | 7.0 |
| Benzyl acetate | 10.0 |
| Oil Bois de Rose | 10.0 |
| Oil Lavender | 20.0 |
| Oil Bergamot rectified | 30.0 |
| 1,3,5-Trimethyl-4-(3-methyl-2-butenyl)-2-cyclohexen-1-ol | 5.0 |
| | 100.0 |

EXAMPLE 31

Tobacco flavor composition

A 1% ethanol solution of 3,5-dimethyl-4-(3-methyl-2-butenyl)-2-cyclohexen-1-one was sprayed on smoking tobacco in an amount sufficient to provide a tobacco composition containing 70 ppm of the flavor additive on a dry basis.

To provide a flavored tobacco which also contained synthetic tobacco, the procedure for the production of a tobacco flavor composition heretofore described in this Example was repeated, except that a synthetic tobacco such as cellulose fibers, for example "CYTREL" (a trademark of the Celenese Chemical Corporation) or "POLYSTREP" (a trademark of Imperial Chemical Corporation) was mixed with the tobacco in a ratio of approximately 1 to 1 by weight.

In a third procedure, a 1% ethanol solution of 3,5-dimethyl-4-(3-methyl-2-butenyl)-2-cyclohexen-1-one was sprayed on synthetic tobacco at the level of 70 ppm on a dry weight basis.

Tobacco flavor compositions prepared by any of the above methods may then be used in the manufacture of cigarettes.

In a panel evaluation against control cigarettes the taste of the flavored cigarettes was described as "light" and woody in character.

EXAMPLE 32

Tobacco flavor composition

A 1% ethanol solution of 3,5-dimethyl-4-(3-methyl-2-butenyl) cyclohexanone was employed at the level of 60 ppm in a similar manner to that described in Example 31.

The taste, as evaluated in cigarettes, was described as possessing a floral and woody character.

EXAMPLE 33

Tobacco flavor composition

By replacing the ketone in Example 31 with 4-(3-methyl-2-butenyl)-5-methyl-2-cyclohexen-1-one at the level of 30 ppm, the taste had a strong cedar character.

What is claimed is:

1. A perfume composition which comprises one or more of the substituted cyclic ketones having the structure:

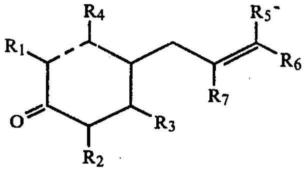

wherein the dotted line may be a carbon-carbon double bond or a carbon-carbon single bond; and wherein each of $R_1$, $R_2$, $R_3$, $R_4$, $R_5$, $R_6$ and $R_7$ may be hydrogen or lower alkyl in an amount effective to impart fragrance thereto in combination with conventional perfume ingredients.

2. The perfume composition of claim 1 wherein the cyclic ketone has the structure:

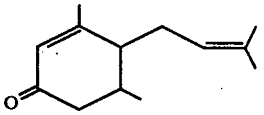

3. The perfume composition of claim 1 wherein the cyclic ketone has the structure:

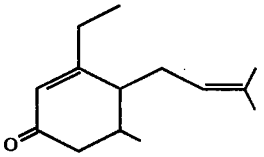

4. The perfume composition of claim 1 wherein the cyclic ketone has the structure:

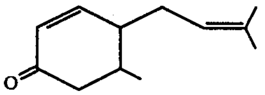

5. The perfume composition of claim 1 wherein the cyclic ketone has the structure:

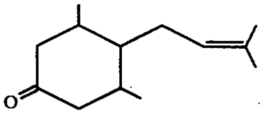

* * * * *

UNITED STATES PATENT AND TRADEMARK OFFICE

CERTIFICATE OF CORRECTION

PATENT NO. : 4,326,996

DATED : April 27, 1982

INVENTOR(S) : Brian J. Willis et al

It is certified that error appears in the above-identified patent and that said Letters Patent are hereby corrected as shown below:

Column 3, lines 39 and 40, "sructures" should read -- structures --

Column 3, line 67, "cyclohexane", second occurrence, should read -- cyclohexene --

Column 4, line 61, the sentence should correctly read -- For example, the concentration of the chemicals of this invention will be from about 0.001 to about 0.1 weight percent in detergents, and from about 0.01 to about 7 weight percent in perfumes and colognes. --

Column 13, line 15, "curous" should read -- cuprous -

Column 15, lines 9 and 10, "Altkylation" should read -- Alkylation --

Signed and Sealed this

*Fifth* Day of *April 1983*

[SEAL]

*Attest:*

GERALD J. MOSSINGHOFF

*Attesting Officer* *Commissioner of Patents and Trademarks*